US009425031B2

(12) United States Patent
Schneider et al.

(10) Patent No.: US 9,425,031 B2
(45) Date of Patent: Aug. 23, 2016

(54) METHOD AND SYSTEM FOR PROVIDING A MODIFIER TO A CURTAIN GAS FOR A DIFFERENTIAL MOBILITY SPECTROMETER

(76) Inventors: Bradley Schneider, Bradford (CA); Thomas Covey, Richmond Hill (CA)

(*) Notice: Subject to any disclaimer, the term of this patent is extended or adjusted under 35 U.S.C. 154(b) by 374 days.

(21) Appl. No.: 12/472,980

(22) Filed: May 27, 2009

(65) Prior Publication Data

US 2009/0294648 A1 Dec. 3, 2009

Related U.S. Application Data

(60) Provisional application No. 61/057,531, filed on May 30, 2008.

(51) Int. Cl.
*H01J 49/04* (2006.01)
*H01J 49/00* (2006.01)
*G01N 27/62* (2006.01)

(52) U.S. Cl.
CPC ............ *H01J 49/004* (2013.01); *G01N 27/624* (2013.01)

(58) Field of Classification Search
CPC .... H01J 49/04; H01J 49/004; H01J 49/0422; H01J 49/0431–49/0454
USPC ................................. 250/281, 282, 288, 289
See application file for complete search history.

(56) References Cited

U.S. PATENT DOCUMENTS

| 6,495,824 | B1 | 12/2002 | Atkinson |
| 6,511,850 | B1* | 1/2003 | Vigh et al. ............... 436/127 |
| 7,026,612 | B2* | 4/2006 | Guevremont et al. ........ 250/288 |
| 7,045,778 | B2* | 5/2006 | Guevremont et al. ........ 250/288 |
| 7,272,512 | B2* | 9/2007 | Wang et al. ................... 702/45 |
| 2005/0133716 | A1* | 6/2005 | Miller et al. ................. 250/293 |
| 2005/0161596 | A1* | 7/2005 | Guevremont ........... H01J 49/04 250/294 |
| 2005/0161597 | A1* | 7/2005 | Guevremont ........ G01N 27/624 250/294 |
| 2005/0218320 | A1* | 10/2005 | Guevremont ........ G01N 27/624 250/292 |
| 2006/0237642 | A1* | 10/2006 | Miller et al. ................. 250/288 |
| 2006/0255261 | A1* | 11/2006 | Whitehouse ........ H01J 49/0431 250/288 |
| 2008/0006769 | A1* | 1/2008 | Staats ........................... 250/288 |

(Continued)

FOREIGN PATENT DOCUMENTS

| WO | WO 0008455 A | * | 2/2000 |
| WO | WO0008455 A | * | 2/2000 |

(Continued)

OTHER PUBLICATIONS

Eiceman et al, "Separation of Ions from Explosives in Differential Mobility Spectrometry by Vapor-Modified Drift Gas", Anal. Chem. 2004, 76, 4937-4944.*

(Continued)

*Primary Examiner* — Nicole Ippolito
*Assistant Examiner* — David E Smith

(57) ABSTRACT

A system including a differential mobility spectrometer is described as is a method of operating the system including the differential mobility spectrometer. The method and system involve a) providing ions to the differential mobility spectrometer; b) providing a drift gas to an inlet of the differential mobility spectrometer; c) adjusting a meter to define a selected volumetric flow rate for supplying a modifier liquid to the drift gas; and, d) supplying an actual volumetric flow rate of the modifier liquid to the drift gas, wherein the actual volumetric flow rate is within a percentage deviation from the selected volumetric flow rate.

16 Claims, 8 Drawing Sheets

(56) References Cited

U.S. PATENT DOCUMENTS

| | | | |
|---|---|---|---|
| 2008/0173809 A1* | 7/2008 | Wu | 250/283 |
| 2009/0174412 A1* | 7/2009 | Atkinson et al. | 324/469 |
| 2010/0282962 A1* | 11/2010 | Machuron-Mandard et al. | 250/282 |

FOREIGN PATENT DOCUMENTS

| | | |
|---|---|---|
| WO | WO0008455 A * | 2/2000 |
| WO | 03/104763 A2 | 12/2003 |
| WO | WO 03104763 A2 * | 12/2003 |
| WO | WO2007/120373 | 10/2007 |

OTHER PUBLICATIONS

International Search Report and Written Opinion, PCT/CA2009/000727; mailed on Sep. 3, 2009.

Extended European Search Report issued Oct. 31, 2011 for Application No. 09753377.2.

Buryakov et al., "A new method of separation of multi-atomic ions by mobility at atmospheric pressure using a high-frequency amplitude-asymmetric strong electric field", International Journal of Mass Spectrometry and Ion Processes 128 p. 143-148 1993.

Krylova N et al., "Effect of Moisture on the Field dependence of Mobility for Gas-Phase ions of organophosphorus compounds at atmospheric pressure with field asymmetric ion mobility spectrometry", J. Phys. Chem. A, 107, p. 3648-3654 2003.

Eiceman, G.A. et al. "Separation of Ions from Explosives in Differential Mobility Spectrometry by vapour-modified drift gas", Anal. Chem., 76, p. 4937-4944, 2004.

Levin, Daren S. et al. "Characterization of Gas-Phase Molecular Interactions on Differential Mobility Ion Behavior Utilizing an Electrospray Ionization-Differential Mobility-Mass Spectrometer System", Anal. Chem., 78, p. 96-106 2006.

\* cited by examiner

METHOD AND SYSTEM FOR PROVIDING A MODIFIER TO A CURTAIN GAS FOR A DIFFERENTIAL MOBILITY SPECTROMETER

This is a non-provisional application of U.S. application No. 61/057,531 filed May 30, 2008. The contents of U.S. application No. 61/057,531 are incorporated herein by reference.

INTRODUCTION

The present invention relates generally to methods and systems relating to a differential mobility spectrometer.

In differential mobility spectrometer systems, a drift gas is typically supplied from a gas source upstream of the differential mobility spectrometer. This drift gas can provide a gas flow through the differential mobility spectrometer. A modifier liquid can be added to the drift gas. Modifiers can be vapors that provide selectivity by clustering with ions to different degrees, thereby shifting these ions differential mobilities. Examples of modifiers can include alcohol such as isopropyl alcohol, water, as well as hydrogen and deuterium exchange agents.

SUMMARY

In accordance with an aspect of a first embodiment of the invention, there is provided a spectrometer system comprising: a) a differential mobility spectrometer for receiving ions from an ion source; b) a drift gas supply for providing a drift gas for flowing through the differential mobility spectrometer; and, c) a modifier supply for supplying an actual volumetric flow rate of a modifier liquid to the drift gas supply, wherein the modifier supply comprises a meter for setting a selected volumetric flow rate, the meter is adjustable to change the selected volumetric flow rate, and the actual volumetric flow rate is within a percentage deviation from the selected volumetric flow rate.

In accordance with an aspect of a second embodiment of the invention, there is provided a method of operating a system including a differential mobility spectrometer. The method comprises a) providing ions to the differential mobility spectrometer; b) providing a drift gas to an inlet of the differential mobility spectrometer; c) adjusting a meter to define a selected volumetric flow rate for supplying a modifier liquid to the drift gas; and, d) supplying an actual volumetric flow rate of the modifier liquid to the drift gas, wherein the actual volumetric flow rate is within a percentage deviation from the selected volumetric flow rate

BRIEF DESCRIPTION OF THE DRAWINGS

The skilled person in the art will understand that the drawings described below are for illustration purposes only. The drawings are not intended to limit the scope of the applicant's teachings in any way.

DETAILED DESCRIPTION OF THE EMBODIMENTS

Figure 1:
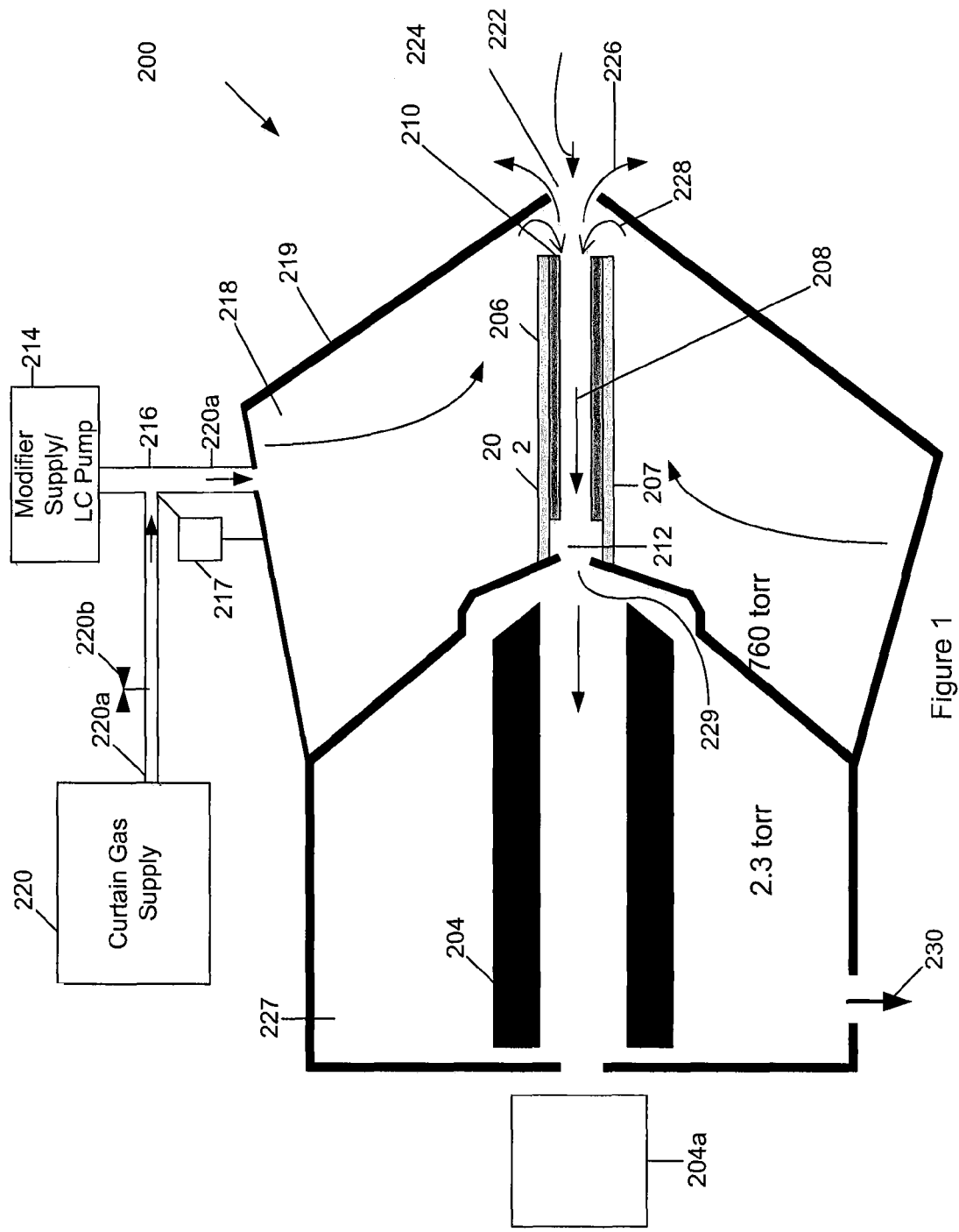
FIG. 1, in a schematic diagram, illustrates a differential mobility spectrometer/mass spectrometer system including a curtain gas supply and a pump for providing a volumetric flow amount of modifier liquid to the curtain gas in accordance with an aspect of a first embodiment of the present invention.

Referring to FIG. 1, there is illustrated in a schematic view, a differential mobility spectrometer/mass spectrometer system 200 in accordance with an aspect of a first embodiment of the present invention. The differential mobility spectrometer/mass spectrometer system 200 comprises a differential mobility spectrometer 202 and a first vacuum lens element 204 of a mass spectrometer (hereinafter generally designated mass spectrometer 204). Mass spectrometer 204 also comprises mass analyzer elements 204a downstream from vacuum chamber 227. Ions can be transported through vacuum chamber 227 and may be transported through one or more additional differentially pumped vacuum stages prior to the mass analyzer indicated schematically as mass analyzer elements 204a. For instance in one embodiment a triple quadrupole mass spectrometer may comprise three differentially pumped vacuum stages, including a first stage maintained at a pressure of approximately 2.3 Torr, a second stage maintained at a pressure of approximately 6 millitorr, and a third stage maintained at a pressure of approximately $10^{-5}$ Torr. The third vacuum stage may contain a detector, as well as two quadrupole mass analyzers with a collision cell located between them. It will be apparent to those with skill in the art that there may be a number of other ion optical elements in the system, which have not been described.

The differential mobility spectrometer 202 comprises plates 206 and electrical insulator 207 along the outside of plates 206. The plates 206 surround a drift gas 208 that drifts from an inlet 210 of the differential mobility spectrometer to an outlet 212 of the differential mobility spectrometer 202. The insulator 207 supports the electrodes and isolates them from other conductive elements. For example, the insulator may be fabricated from ceramic or Teflon™. The outlet 212 of the differential mobility spectrometer 202 releases the drift gas that may flow into an inlet 229 of the vacuum chamber 227 and mass spectrometer 204.

The differential mobility spectrometer 202 is contained within a curtain chamber 218, defined by a curtain plate or boundary member 219, and supplied with a curtain gas from a curtain gas supply 220. Specifically, curtain gas from curtain gas supply 220 can flow through curtain gas conduit 220a at flow rates determined by flow controller 220b. The system 200 also comprises a LC pump and modifier supply 214 for pumping precise amounts of a modifier liquid into the curtain gas conduit 220a at T-juncture 216. Specifically, LC pump 214 comprises a meter (not shown), which can be changed to set a selected volumetric flow rate of the modifier liquid into the juncture 216. Based on this adjustment of the meter, the LC pump 214 is then operable to provide an actual volumetric flow rate of the modifier liquid to the juncture 216 and into curtain gas conduit 220a to mix with the curtain gas.

It will be apparent to those of skill in the art that LC pump 214 could be replaced with a syringe pump or other accurately controllable dispensing devices for dispensing the modifier liquid. Whatever dispensing device is used, this device can be sufficiently accurate such that the actual volumetric flow rate is within a relatively small percentage deviation of the selected volumetric flow rate. For example, this percentage deviation may be as little as 2% of the selected volumetric flow rate, or even as little as 0.2% of the selected volumetric flow rate. This actual volumetric flow rate and small percentage deviation can be maintained for hours or days as required. Again, during this dispensing period, which may be as little as an hour, or as long as several days, the percentage deviation can be maintained below at least 2%, and possibly below 0.2% of the selected volumetric flow rate.

The differential mobility spectrometer 202 is contained within a curtain chamber 218 defined by a curtain plate or boundary member 219 and supplied with the curtain gas from the curtain gas supply 220 via curtain gas conduit 220a. When the curtain gas is released into the curtain chamber by the curtain gas conduit 220a, it can contain a precisely metered quantity of modifier liquid from LC pump 214. Ions 222 are provided from an ion source (not shown) and are emitted into the curtain chamber 218 via curtain chamber inlet 224. The pressure of the curtain gases in the curtain chamber 218 can be maintained at or near 760 Torr. This pressure can provide both a curtain gas outflow 226 out of curtain gas chamber inlet 224, as well as a curtain gas inflow 228 into the differential mobility spectrometer 202, which inflow 228 becomes the drift gas 208 that carries the ions 222 through the differential mobility spectrometer 202 and into the vacuum chamber 227. As the curtain gas within the curtain chamber 218 can include a precise proportion of modifier liquid by carefully controlling the flow controller 220b and LC pump 214, the drift gas 208 can also comprise a precisely determined percentage of modifier. Optionally, the system 200 may comprise a mixing chamber instead of, or in addition to, the curtain chamber. This mixing chamber could be located in the curtain gas conduit 220a upstream from the differential mobility spectrometer. In such an embodiment, the mixing chamber could facilitate mixing of the modifier liquid and the curtain gas.

As illustrated in FIG. 1, the first vacuum lens element 204 of the mass spectrometer 204 can be contained within a vacuum chamber 227, which vacuum chamber can be maintained at a much lower pressure than the curtain chamber 218. In accordance with an aspect of an embodiment of the present invention, the vacuum chamber 227 can be maintained at a pressure of 2.3 Torr by a vacuum pump 230 while the curtain chamber 218 and an internal operating pressure of the differential mobility spectrometer 202 can be maintained, as mentioned above, at a pressure of about 760 Torr.

Optionally, either or both of juncture 216 and curtain chamber 218 can include a heater 217 for heating the mixture of the curtain gas and the modifier liquid to further control the proportion of modifier liquid in the curtain gas.

Figure 2:
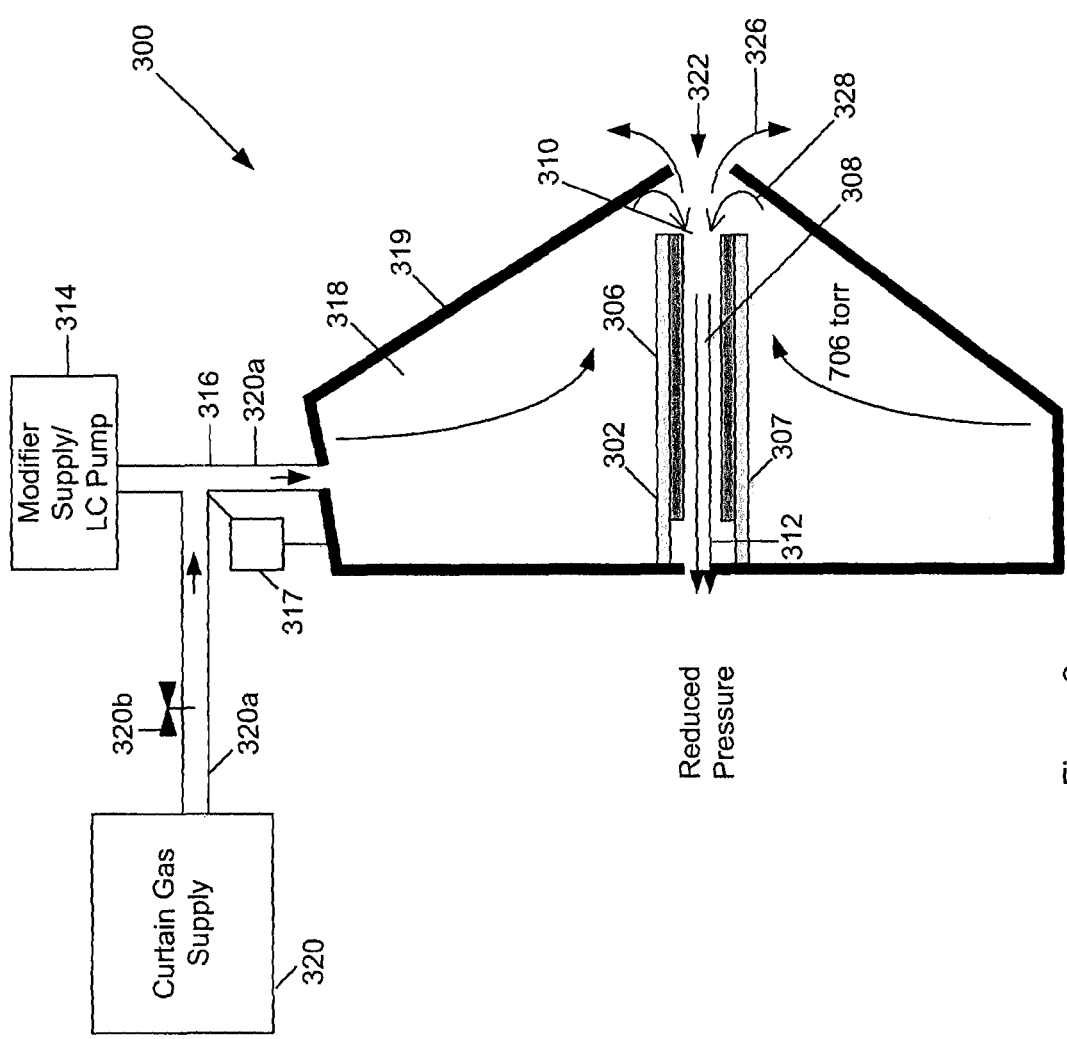
FIG. 2, in a schematic view, illustrates a differential mobility spectrometer including a curtain gas supply and a pump for providing a volumetric flow amount of modifier liquid to the curtain gas in accordance with an aspect of a second embodiment of the present invention.

Referring to FIG. 2, there is illustrated in a schematic diagram, a differential mobility spectrometer system 300 in accordance with an aspect of a second embodiment of the present invention. For clarity, elements of the system 300 of FIG. 2 that are analogous to elements of the system 200 of FIG. 1 are designated using the same reference numerals as in FIG. 1, with 100 added. For brevity, the description of FIG. 1 is not repeated with respect to FIG. 2.

As shown, the differential mobility spectrometer system 300 of FIG. 2 resembles a portion of the system 200 of FIG. 1, but lacks the mass spectrometer and vacuum chamber elements of FIG. 1. Accordingly, the differential mobility spectrometer 300 of FIG. 2 can be installed upstream of any number of different mass spectrometer elements, or may simply be installed upstream of a region of reduced pressure, as shown, which draws the ions 322 and drift gas 308 through the differential mobility spectrometer 302. Alternatively, there may be a detector downstream of the outlet of the differential mobility spectrometer 302 such as a Faraday cup or other ion current measuring device.

The differential mobility spectrometer 302 is contained within a curtain chamber 318. The curtain chamber 318 is supplied with a curtain gas from a curtain gas supply 320 in a manner similar to that described above in connection with FIG. 1.

Figure 3:
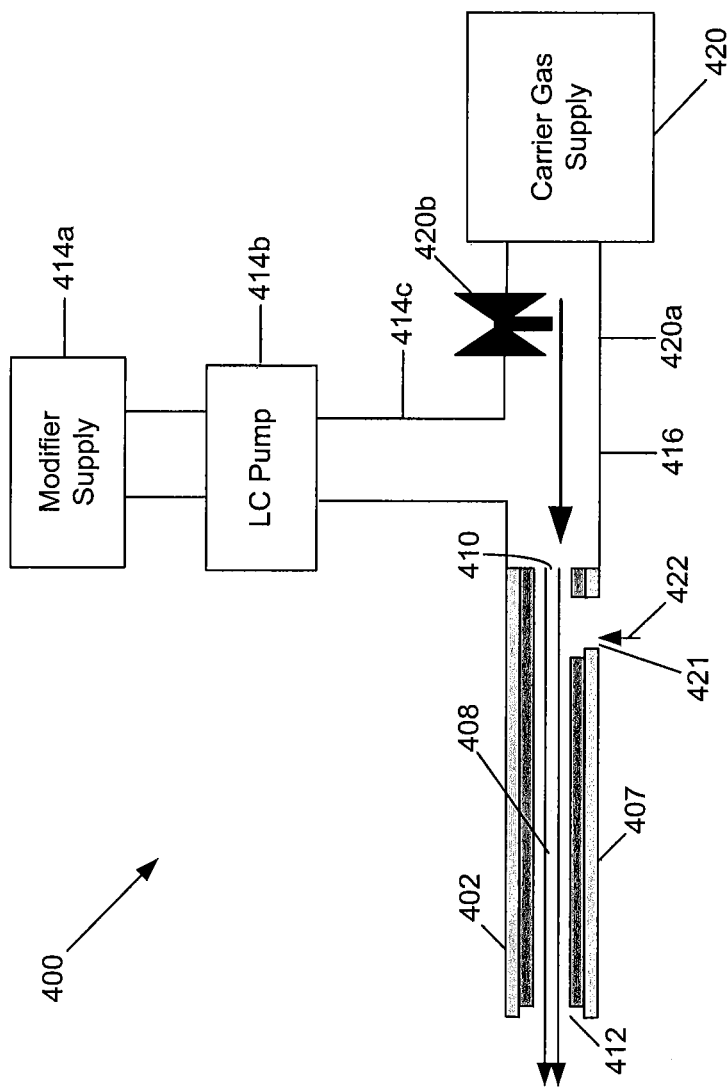
FIG. 3, in a schematic view, illustrates a differential mobility spectrometer including a gas supply and a pump for providing a volumetric flow amount of modifier liquid to the gas in accordance with an aspect of a third embodiment of the present invention.

Referring to FIG. 3, there is illustrated in a schematic view, a differential mobility spectrometer system 400 in accordance with an aspect of a third embodiment to the present invention. For clarity, elements of the system 400 of FIG. 3 that are analogous to corresponding elements of the system 300 of FIG. 2 are designated using the same reference numerals, with 100 added. For brevity, the descriptions of FIGS. 1 and 2 are not repeated with respect to FIG. 3.

The differential mobility spectrometer 400 of FIG. 3 is even simpler than the system 300 of FIG. 2 in that a differential mobility spectrometer 402 of the system 400 is not contained within a curtain chamber.

As shown, a carrier or drift gas supply 420 can supply a carrier gas to the differential mobility spectrometer 402 via carrier gas conduit 420a. The carrier gas can flow at flow rates determined by a flow controller 420b. At juncture 416, the carrier gas conduit 420a is coupled to a modifier liquid supply conduit 414c. Modifier Liquid can be pumped into the carrier gas conduit 420a by LC Pump 414b, which itself draws the modifier liquid from modifier supply 414a. Downstream of juncture 416, the carrier gas mixed with the modifier liquid can flow into the differential mobility spectrometer 402 via inlet 410 to become the drift gas 408. Ions 422 are released into the differential mobility spectrometer 402 via side inlet 421.

Figure 4:
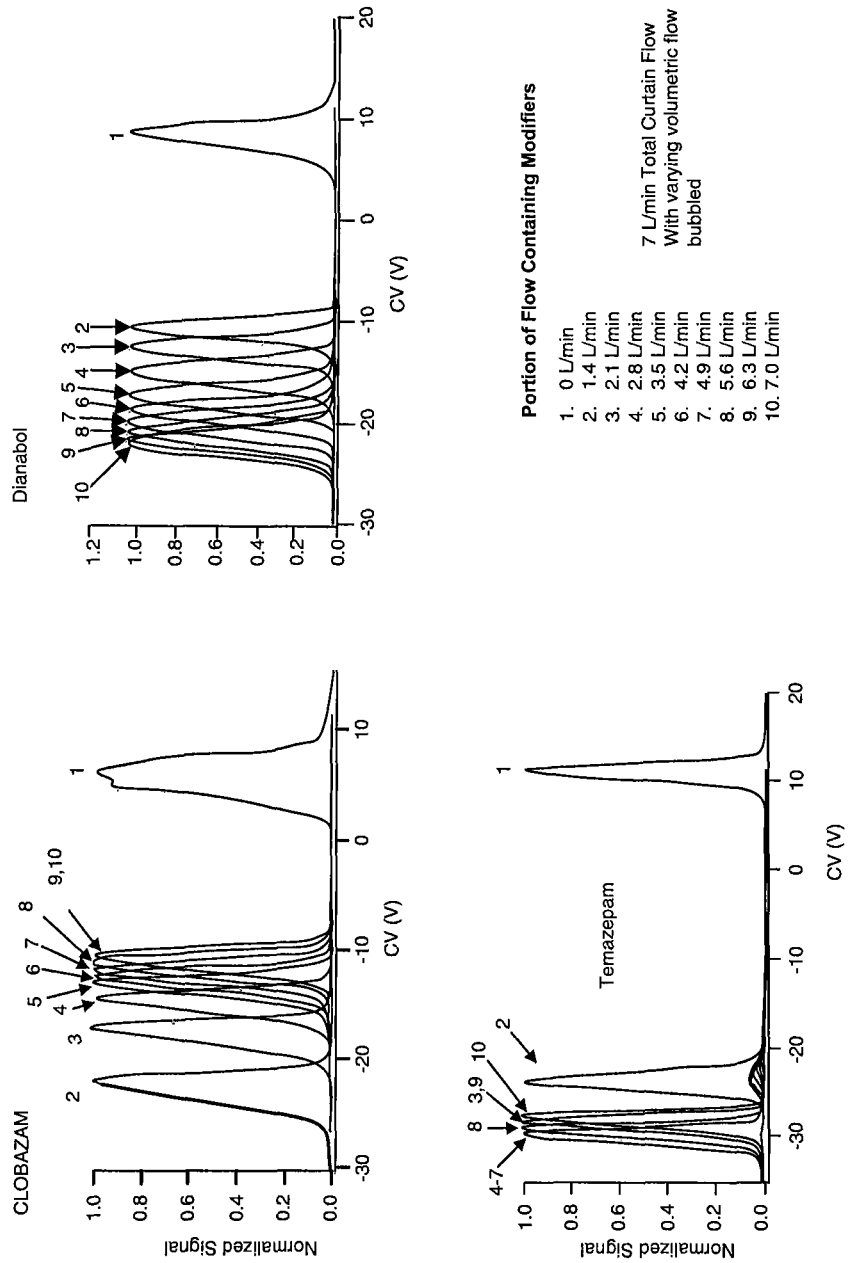
FIG. 4 illustrates CV scans for three different compounds as the concentration of a modifier added to a curtain gas increases.

Referring to FIG. 4, CV scans for 3 different compounds as the concentration of a particular modifier, 2-propanol, provided to the curtain gas by the LC pump 214 changes are illustrated. For these data, the total curtain gas inflow to the curtain chamber 218 was maintained substantially constant at 7 L/min. The 3 compounds are Clobazam, Dianabol and Temazepam.

In the case of each of these compounds, it is clear that the concentration of modifier in the curtain gas has a dramatic effect on CV peak position. This is most apparent as the proportion of modifier liquid increases from 0 L/min to 1.4 L/min, which results in a dramatic leftward shift in the peak. In the case of Dianabol, subsequent increases in the proportion of modifier liquid will shift the peaks further leftward; however, in the case of Clobazam and Temazepam, further increases in the proportion of modifier appear to shift the peak toward the right—that is, back toward the peak for trace one, albeit only part way.

More specifically, referring to the graph for Clobazam, the first trace, designated 1, is shown far to the right, with a peak at approximately 6 volts. Trace 1 represents the case in which no modifiers are contained within the curtain flow. Then, when the portion of curtain flow containing the modifier increases to 1.4 L/min, the peak shifts sharply to the left, such that the peak of trace 2, is located somewhere between −20 and −25 volts. Perhaps somewhat counter intuitively, however, as the portion of the curtain flow containing the modifier is further increased, the resulting traces 3 to 10 shift progressively rightward again, such that the voltage for each of these peaks monotonically increases as the portion of flow containing modifiers increases from 2.1 L/min.

The situation is otherwise in the case of Dianabol. Specifically, trace 1, representing no Modifier liquids included within the curtain flow, is far to the right, with a peak slightly below 10 volts. When the portion of flow containing modifiers is increased to 1.4 L/min, the peak shifts sharply to the left, such that the peak of trace 2 is slightly below −10 volts. As the portion of flow containing modifiers is further increased, the peaks shift further leftward, such that the peaks for traces 7 to 10 are all below −20 volts.

In the case of Temazepam the situation is more complicated. Again, trace 1 representing the case in which no modifier is added to the curtain flow has a peak of slightly above 10 volts. Then, when the portion of flow containing modifiers is increased to 1.4 L/min, the peak shifts sharply leftward to trace 2, having a peak somewhere between −25 volts and −22 volts. Further increasing the portion of flow containing modifiers from 1.4 L/min to 2.8 L/min shifts the peaks of the resulting traces further leftward, such that the peak of trace 4 is around −30 volts. However, increasing the portion of flow containing modifiers from 2.8 L/min to 4.9 L/min leaves the peaks for the resulting traces substantially unchanged in position. Further increasing the portion of flow containing modifiers from 4.9 L/min to 7.0 L/min can, as shown by traces 8, to 10, shift the resulting peaks of these traces gradually rightward, such that the peak for trace 10, representing 7.0 L/min containing modifiers, is now above −30 volts.

The control of the modifier introduction rate to the curtain gas can be very important to achieve reproducible mobility peak positions. This contention is supported by all of the graphs of FIG. 4, which show how peak position can shift greatly, and perhaps surprisingly, based on the proportion of modifier liquid within the curtain gas. Given that CV scans can continue for hours, or even days, if there is significant uncontrolled variation in the proportion of modifier liquid added to the curtain gas, then there can be a very significant drift of the CV position for the compound of interest over this selected time interval, be it measured in hours or days. This can be highly problematic as for quantitative analyses, the CV can be tuned at the start of runs and fixed for the duration at the initial optimum (i.e. at the initial peak). If the drift in CV position is sufficient, then the actual measured signal can drop by a significant factor, despite the shifted peak height being substantially the same as the height of the initial peak.

Figure 5:
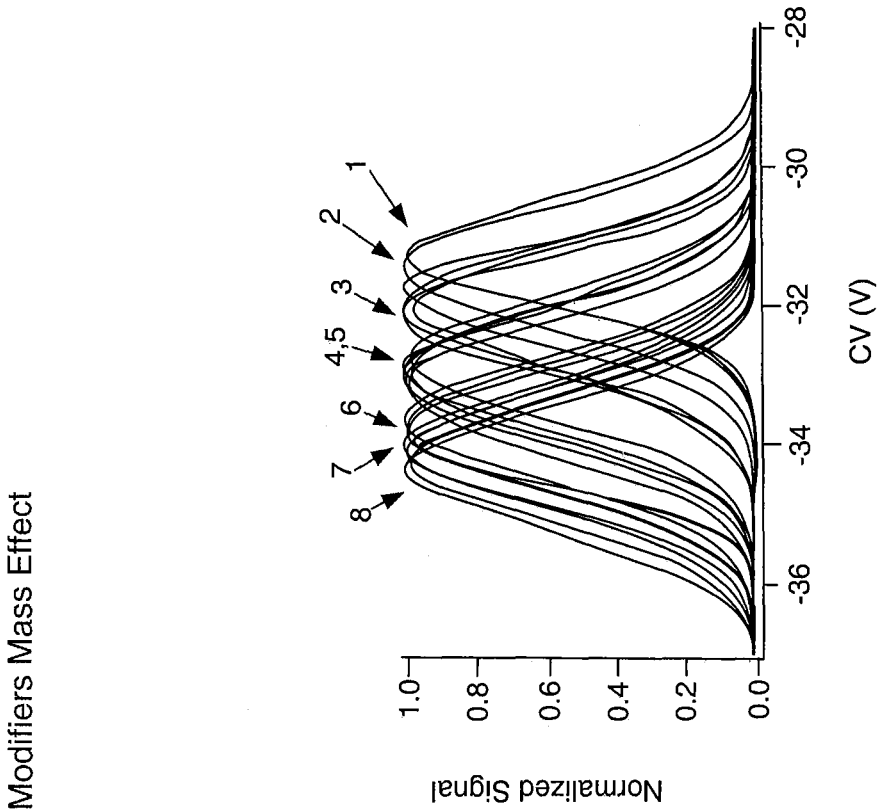
FIG. 5 illustrates CV scans for Temazepam where the entire curtain gas flow is bubbled through 2-propanol such that the proportion of modifier liquid contained within the curtain gas remains substantially the same, but the absolute quantity of modifier liquid introduced to the drift gas increases with the increases in the total curtain gas flow rate.

Referring to FIG. 5, there are illustrated CV scans for Temazepam where the entire curtain gas flow is bubbled through 2-propanol (the modifier liquid). In this case, the proportion of modifier liquid contained within the curtain gas remains substantially the same; however, the total curtain gas flow rate changes to vary the mass of the modifier liquid introduced to the drift gas. Again, the observed CVs for Temazepam vary with the total curtain gas flow rate, and as a result the total modifier flow rate, despite the proportion of modifier remaining constant.

More specifically, as shown, the first trace, representing curtain gas flow rates of 2 L/min has a peak at approximately −31 volts. Then, as the curtain gas flow rate increases and the resulting quantity of modifier liquid increases, the traces migrate leftward, until trace 8, representing a curtain gas flow rate of 25 L/min (and a correspondingly larger amount of modifier liquid) has a peak at somewhere between −35 and −34 volts. Traces 2-7 represent, respectively, curtain gas flow rates of 5 L/min, 8 L/min, 11 L/min, 14/min, 17 L/min and 20 L/min. Differential mobility separation occurred with 4300 volts applied in all cases.

Figure 6:
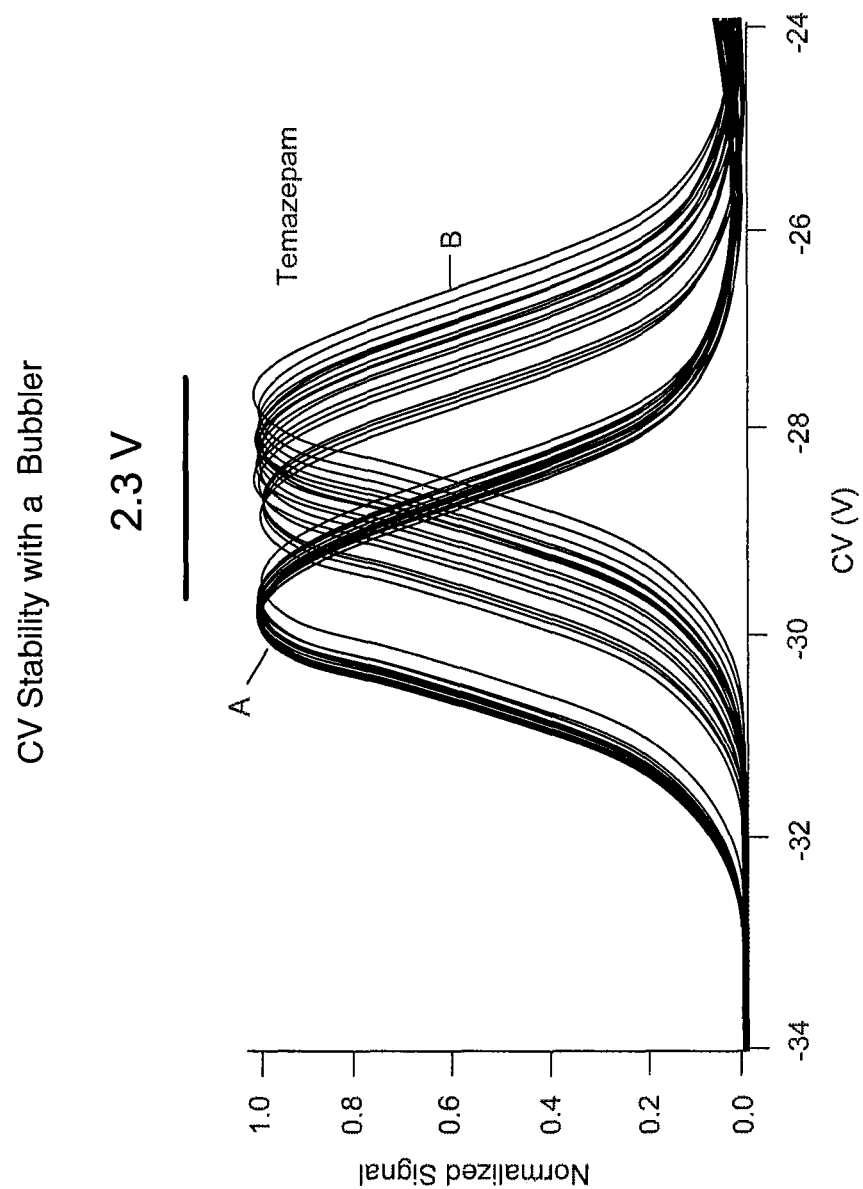
FIG. 6 illustrates CV scans for Temazepam with bubbling of the curtain gas through a modifier liquid.

Referring to FIG. 6, CV scans for Temazepam measured over approximately a six hour time period with bubbling of the curtain gas through a liquid modifier prior to introduction to the curtain chamber is illustrated. As illustrated in FIG. 6, variation in bubbler results can cause a significant drift of this CV position for this compound over a six hour time period. This can be problematic because for quantitative analysis the CV could be tuned at the start of the run and fixed for duration at the initial optimum (which appears to be approximately −28.4 volts in FIG. 6). The drift in CV position shown in FIG. 6 could be unacceptable, as particularly for the six hour time point data, a CV of −28.4 volts would drop the measured signal by more than a factor of 2. Considering a full spread in CV optimum demonstrated in FIG. 6 (in particular the trace for the three hour time period, designated A, and the trace for the six hour time period, designated B) there could be a drop by a factor of 10 in the signal with this range of CV spread of approximately 2.3 volts.

Figure 7:
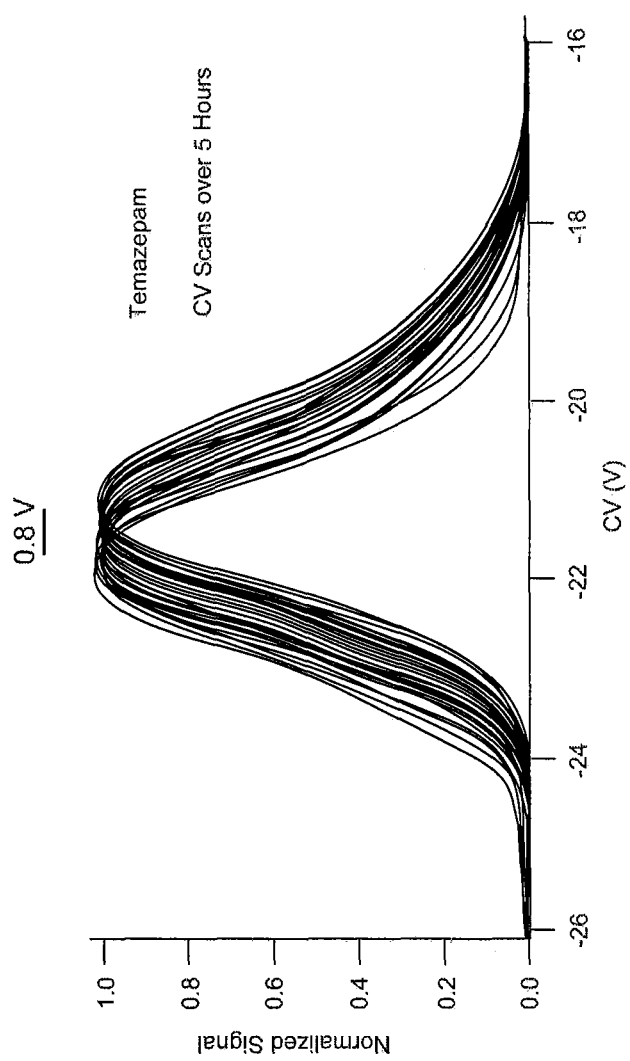
FIG. 7 illustrates CV scans for Temazepam in which a substantially fixed amount of 2-propanol is dispensed into a curtain gas flow for a five hour time period.

Referring to FIG. 7, there are illustrated CV scans for Temazepam measured over a five hour time period. In this case, 50 uL/min of 2-propanol was dispensed into approximately 7.7 L/min of curtain gas flow for the five hour period. As can be seen from FIG. 7, the CV reproducibility for Temazepam was much better than what was observed with the bubbler demonstrating a full spread of approximately 0.8 volts. In this case, the decrease in signal for Temazepam due to CV drift was less than 10 percent over the course of these experiments. Based on the foregoing, it appears that accurately and precisely dispensing modifier liquids into the drift gas stream for a differential mobility spectrometer system can help quantitative analysis in the presence of modifiers. These results can be further improved by heating to improve reproducibility.

Figure 8:
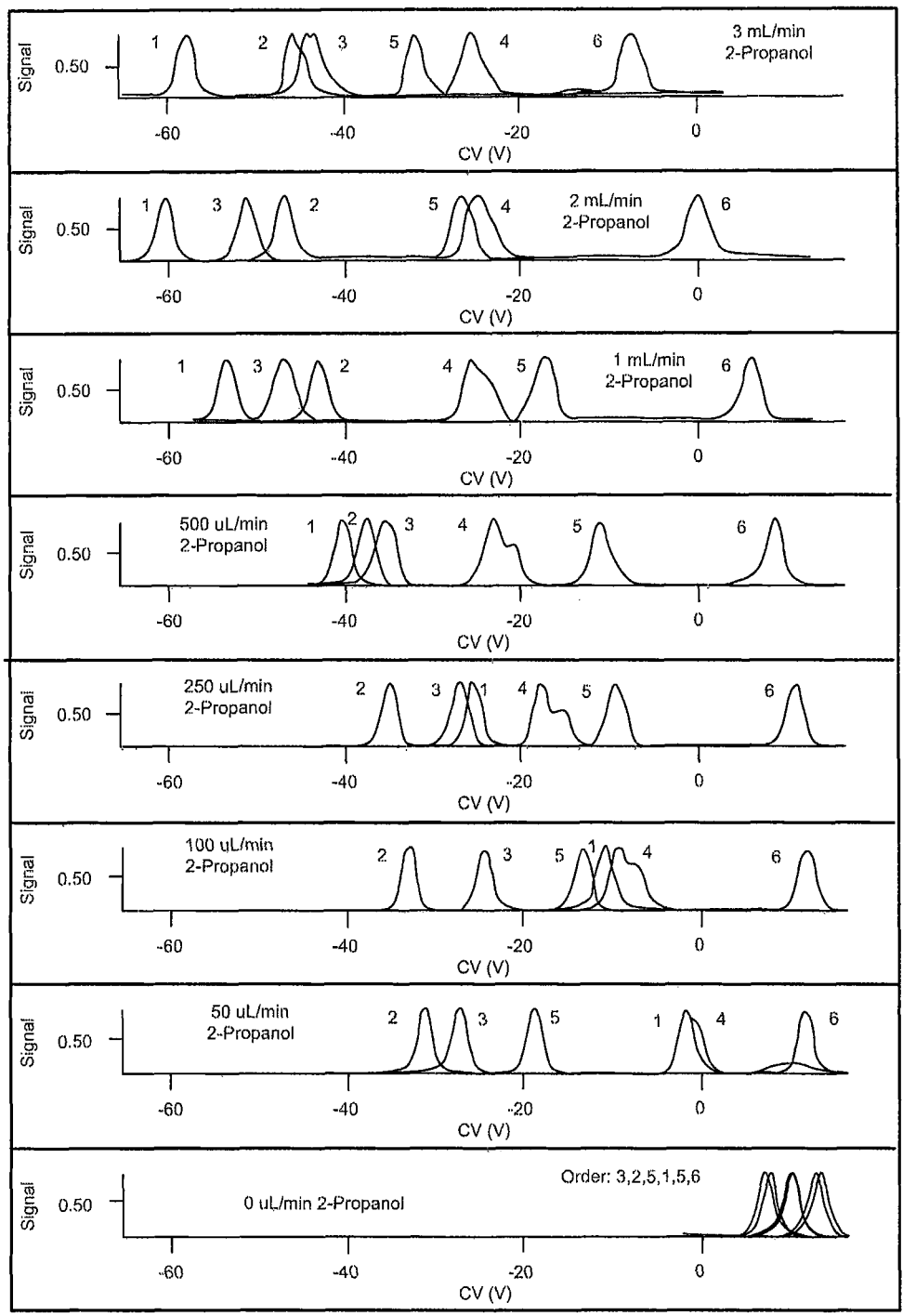
FIG. 8 illustrates, in a series of panes, mobility CV scans for 6 isobaric compounds with different volumetric flow rates of modifier liquid.

Referring to FIG. 8, there is illustrated in a series of panes, mobility CV scans for 6 isobaric compounds (m/z 316). Specifically, FIG. 8 illustrates how selectivity can be tuned using modifier flow rates. Traces for six isobaric compounds are numbered as follows: 1. Bromazepam, 2. Clonazepam, 3. Oxfendazole, 4. Chlorprothixene, 5. Flusilazole, 6. Pamaquine. The lowest pane, pane A, shows DMS separation with 4200 volts applied and a total curtain gas flow rate of 11.9 L/min, with no modifier added. The remainder of the panes, panes B to H, show the effect on selectivity as the volumetric flow of 2-propanol modifier into the curtain gas increases. Increasing the volumetric flow of modifier liquid tends to increase the peak capacity by spreading the peaks over a larger range of CVs; however, the best overall separation shown for the six isobaric compounds is actually achieved in pane F when the modifier flow rate is 1 mL/min, rather than at higher settings. For example, peaks 4 and 5 in pane F, representing chlorprothixene and flusilazole respectively, can be more readily distinguished than the peaks of traces 4 and 5 in pane G when the modifier flow rate is 2 mL/min. Traces 2 and 3, representing Clonazepam and Oxfendazole respectively, are more readily distinguishable in pane C, representing modifier flow rates of 100 uL/min, and in pane G, representing modifier flow rates of 2 mL/min, than they are in pane F. However, in both of these panes it is much more difficult to distinguish peaks 4 and 5, while in pane F, it is still possible to distinguish peaks 2 and 3 by selecting high enough on the peaks to exclude the bottom portion at which they overlap.

Accordingly, using the data of the type illustrated in panes A to H, selectivity can be enhanced by carefully controlling the amount of modifier liquid added. That is, gradually larger amounts of modifier liquid can be added, and the effect on selectivity observed, such that once adding additional amounts of modifier liquid starts to diminish selectivity, further increases in modifier liquid can be stopped.

Other variations and modifications of different embodiments of the present invention are possible. For example, it will be apparent to those of skill in the relevant arts that the foregoing approaches can be applied to both planar and cylindrical field asymmetric wave form ion mobility spectrometer (FAIMS) devices. All such modifications or variations are believed to be within the sphere and scope of aspects of embodiments of the invention as defined by the claims appended hereto.

The invention claimed is:

1. A spectrometer system comprising:
an ion source for generating ions;
a differential mobility spectrometer having an inlet and an outlet, the differential mobility spectrometer being situated downstream from said ion source for receiving ions from the ion source;
a boundary member that surrounds the differential mobility spectrometer so as to define a curtain chamber, the inlet of the differential mobility spectrometer opening up into the curtain chamber, the outlet of the differential mobility spectrometer being configured so as to allow the ions to exit the curtain chamber;
a curtain gas supply that provides a curtain gas at substantially atmospheric pressure, the curtain gas supply comprising a curtain gas conduit;
a modifier supply that provides a modifier liquid, the modifier supply comprising a modifier conduit;
a junction for merging the modifier conduit into the curtain gas conduit;
the curtain gas conduit being fluidly connected downstream of the junction to the curtain chamber;
a heater positioned inside the curtain chamber for heating the modifier liquid and the curtain gas;
wherein said boundary member directs at least a portion of the curtain gas to the inlet of the differential mobility spectrometer so as to become a drift gas; and,
wherein the modifier supply also comprises a meter for setting a selected volumetric flow rate of the modifier liquid, the meter being adjustable to change the selected volumetric flow rate, and the modifier supply being capable of maintaining an actual continuous volumetric flow rate that enters the curtain gas that is within a precision of about 2 percent of the selected volumetric flow rate.

2. The spectrometer system as defined in claim 1 wherein the actual volumetric flow rate is within a precision of 0.2 percent of the selected volumetric flow rate.

3. The spectrometer system as defined in claim 1 wherein the modifier supply comprises a pump for supplying the actual volumetric flow rate of the modifier liquid to the curtain gas.

4. The spectrometer system as defined in claim 1 further comprising a mass spectrometer in fluid communication with the differential mobility spectrometer for receiving the ions from the differential mobility spectrometer.

5. The spectrometer system as defined in claim 4 further comprising a detector for detecting the ions received by the mass spectrometer.

6. The spectrometer system as defined in claim 1 wherein the differential mobility spectrometer comprises one of straight and curved electrodes.

7. The spectrometer system as defined in claim 1 wherein the modifier supply is capable of maintaining the actual volumetric flow rate with a precision of better than about 0.2 percent.

8. The spectrometer system of claim 1 wherein the concentration of said modifier liquid in said curtain gas in the curtain gas conduit downstream of the junction is at least 1%.

9. A method of operating a system including a differential mobility spectrometer, the method comprising:
a) creating ions in an ion source and transporting the ions from the ion source to an inlet of the differential mobility spectrometer, the inlet being disposed downstream from the ion source;
b) providing a boundary member that surrounds the differential mobility spectrometer so as to define a curtain chamber, an inlet of the differential mobility spectrometer opening up into the curtain chamber, the outlet of the differential mobility spectrometer being configured so as to allow the ions to exit the curtain chamber;
c) providing a curtain gas supply that provides a curtain gas at substantially atmospheric pressure, the curtain gas supply comprising a curtain gas conduit;
d) providing a modifier supply that provides a modifier liquid, the modifier supply comprising a modifier conduit;
e) providing a junction for merging the modifier conduit into the curtain gas conduit;
the curtain gas conduit being fluidly connected downstream of the junction to the curtain chamber;
f) heating the modifier liquid and the curtain gas in the curtain chamber;
g) directing at least a portion of the curtain gas to the inlet of the differential mobility spectrometer so as to become a drift gas
h) adjusting a meter to define a selected volumetric flow rate for supplying a modifier liquid to the curtain gas; and,
i) supplying an actual volumetric flow rate of the modifier liquid continuously to the curtain gas over a selected time interval of an analysis, wherein the actual volumetric flow rate that enters the curtain gas over the selected time interval is within a precision of about 2 percent of the selected volumetric flow rate and the concentration of said modifier liquid in said curtain gas is at least 1%.

10. The method as defined in claim 9 wherein i) comprises providing the actual volumetric flow rate over a selected time interval and wherein the actual volumetric flow rate is within a precision of 0.2 percent of the selected volumetric flow rate over the selected time interval.

11. The method as defined in claim 9 wherein i) comprises pumping the actual volumetric flow rate of the modifier liquid to the curtain gas.

12. The method as defined in claim 9 further comprising
j) transmitting the ions from the differential mobility spectrometer; and
k) detecting the ions transmitted from the differential mobility spectrometer.

13. The method as defined in claim 12 further comprising
l) determining a defined volumetric flow rate of the modifier to the curtain gas to provide a selected degree of separation of the ions;
wherein i) comprises setting the selected volumetric flow rate to equal the defined volumetric flow rate.

14. The method as defined in claim 13, wherein l) comprises over a plurality of time intervals, adjusting the actual volumetric flow rate of modifier added to the curtain gas such that a plurality of different volumetric flow rates of modifier are provided to the curtain gas during the plurality of time intervals such that a different amount of modifier is provided during each time interval in the plurality of time intervals;
determining a plurality of degrees of selectivity by, during each time interval and for each different amount of modifier, detecting the ions to determine an associated degree of selectivity;
and,
selecting the selected volumetric flow rate based on the plurality of degrees of selectivity and the plurality of different volumetric flow rates.

15. The method as defined in claim 9 wherein the selected time interval is at least one hour.

16. The method as defined in claim 9 wherein the actual volumetric flow rate is maintained with a precision of better than about 0.2 percent.

* * * * *